(12) United States Patent
Melvin, Jr. et al.

(10) Patent No.: US 8,217,155 B2
(45) Date of Patent: Jul. 10, 2012

(54) METABOLITES AND DERIVATIVES OF AMBRISENTAN

(75) Inventors: Lawrence S. Melvin, Jr., Longmont, CO (US); Martina Ullrich, Schriesheim (DE); Hans-Guenther Hege, Neustadt (DE); Jürgen Weymann, Bad Dürkheim (DE)

(73) Assignees: Gilead Colorado, Inc., Boulder, CO (US); Abbott GmbH & Co. KG, Wiesbaden (DE)

( * ) Notice: Subject to any disclaimer, the term of this patent is extended or adjusted under 35 U.S.C. 154(b) by 211 days.

(21) Appl. No.: 12/671,439

(22) PCT Filed: Jul. 31, 2008

(86) PCT No.: PCT/US2008/009236
§ 371 (c)(1),
(2), (4) Date: Jan. 29, 2010

(87) PCT Pub. No.: WO2009/017777
PCT Pub. Date: Feb. 5, 2009

(65) Prior Publication Data
US 2010/0204163 A1    Aug. 12, 2010

Related U.S. Application Data

(60) Provisional application No. 60/953,053, filed on Jul. 31, 2007.

(51) Int. Cl.
*C07H 17/02* (2006.01)
*C07D 239/02* (2006.01)

(52) U.S. Cl. ........ 536/17.4; 544/302; 544/315; 544/318
(58) Field of Classification Search .................. 536/17.4; 544/302, 315, 318
See application file for complete search history.

(56) References Cited

U.S. PATENT DOCUMENTS

| | | | |
|---|---|---|---|
| 7,109,205 B2 * | 9/2006 | Riechers et al. | 514/274 |
| 2004/0092742 A1 | 5/2004 | Riechers et al. | 514/274 |
| 2008/0139483 A1 | 6/2008 | Gorcynski et al. | 514/183 |
| 2008/0139593 A1 | 6/2008 | Gerber et al. | 514/183 |
| 2009/0054473 A1 | 2/2009 | Roden et al. | 514/2 |
| 2010/0152217 A1 | 6/2010 | Gerber et al. | 514/183 |

FOREIGN PATENT DOCUMENTS

| | | |
|---|---|---|
| CA | 2669535 | 6/2008 |
| CA | 2669536 | 6/2008 |
| DE | 19726146 | 12/1998 |
| DE | 19806438 | 8/1999 |
| WO | WO 96/11914 | 4/1996 |
| WO | WO 2008/073927 | 6/2008 |
| WO | WO 2008/073928 | 6/2008 |
| WO | WO 2009/017777 | 2/2009 |
| WO | WO 2009/026517 | 2/2009 |
| WO | WO 2010/062640 | 6/2010 |

OTHER PUBLICATIONS

Galié (2005) "Ambrisentan long-term safety and efficacy in pulmonary arterial hypertension I-Year follow-up", ATS May 23, 2005.
Galié et al. (2005), "Ambrisentan therapy for pulmonary arterial hypertension", *J. Am. Coll. Cardiol.*, 46(3): 529-535.
International Search Report and Written Opinion in PCT/US2008/009236 dated Feb. 20, 2009.
Jansen et al. (2001), "Structural similarity and its surprises: endothelin receptor antagonists—process research and development report", *Organic Process R&D* 5: 16-22.
Myogen, Inc. News Release, Dec. 4, 2003 (http://www.pmewswire.com/cgi-bin/stories.pl?ACCT=104&STORY=/www/story/12-04-2003/0002069898&EDATE=).
Myogen, Inc. News Release, Jan. 8, 2004 (http://investor.myogen.com/phoenix.zhtml?c=135160&p=irol-newsArticle&ID=759080&highlight=).
Myogen, Inc. News Release, Feb. 16, 2004 (http://investor.myogen.com/phoenix.zhtml?c=135160&p=irol-newsArticle&ID=759478&highlight=).
Myogen, Inc. News Release, May 24, 2004 (http://investor.myogen.com/phoenix.zhtml?c=135160&p=irol-newsArticle&ID=759469&highlight=).
Myogen, Inc. News Release, Feb. 10, 2005 (http://investor.myogen.com/phoenix.zhtml?c=135160&p=irol-newsArticle&ID=759971&highlight=).
Myogen, Inc. News Release, May 19, 2005 (http://investor.myogen.com/ phoenix.zhtml?c=135 160&p=irol-newsArticle&ID=759658&highlight=).
Riechers et al. (1996), "Discovery and optimization of a novel class of orally active nonpeptidic endothelin-A receptor antagonists", *Journal of Medicinal Chemistry*, 39: 2123-2138.
Rubin (2004) "Ambrisentan improves exercise capacity and clinical measures in pulmonary arterial hypertension", ATS May 21-26, 2004.
Rubin et al. (2005), "Ambrisentan for pulmonary arterial hypertension", *Future Cardiol.* 1(4): 1-8.
Sorbera et al. (2005), "Ambrisentan", *Drugs of the Future* 30(8): 765-770.

* cited by examiner

*Primary Examiner* — Elli Peselev
(74) *Attorney, Agent, or Firm* — Harness, Dickey & Pierce, P.L.C.; J. Timothy Keane; Kisuk Lee

(57) ABSTRACT

The invention relates to derivatives and metabolites of ambrisentan, including compounds of general Formula (I)

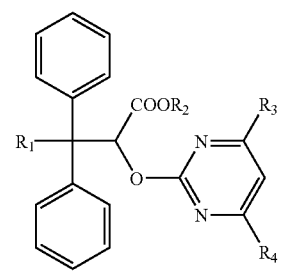

or salts, hydrates, solvates, racemates, or optical isomers thereof, wherein $R^1$ is —OH or —OCH$_3$; $R^2$ is —H, lower alkyl (e.g. $C_1$-$C_4$ alkyl) or glycosidyl; and $R^3$ and $R^4$ are independently —CH$_3$, —C(O)H or —CH$_2$OR$^6$, wherein $R^6$ is —H or a hydrocarbyl group having 1 to 20 carbon atoms.

5 Claims, 2 Drawing Sheets

METABOLITES AND DERIVATIVES OF AMBRISENTAN

CROSS REFERENCE TO RELATED APPLICATIONS

This is a national phase application of PCT International Application No. PCT/US2008/009236, filed 31 Jul. 2008 (Publication No. WO 2009/017777), which claims priority to U.S. application Ser. No. 60/953,053, filed 31 Jul. 2007. The entire disclosures of the above applications are incorporated herein by reference.

FIELD

The present teachings relate to metabolites and derivatives of ambrisentan, a selective endothelin receptor antagonist (ERA).

BACKGROUND

Endothelins are a family of peptides synthesized and released by endothelial cells in the vascular system, lung, kidney, gastrointestinal cells, and macrophages. The endothelin family is comprised of three 21-α-amino acid isopeptides (ET-1, ET-2, and ET-3). Endothelin-1 (ET-1) has been identified as the major cardiovascular isopeptide.

ET-1 acts in an autocrine and paracrine manner through type A ($ET_A$) and type B ($ET_B$) endothelin receptor subtypes. $ET_A$ receptors are located on vascular smooth muscle cells and their activation mediates vasoconstriction and mitogenesis. $ET_B$ receptors are primarily located on endothelial cells, where they stimulate vasodilation via activation of endothelial cell nitric oxide synthesis and ET-1 clearance via receptor-mediated endocytosis. However, some $ET_B$ receptors are also located on smooth muscle cells where they mediate vasoconstriction and cellular proliferation. $ET_A$ receptor activation is also a powerful stimulus for cardiac myocyte hypertrophy and fibroblast proliferation in the kidneys.

In human blood vessels, 85% of the ET receptor population is made up of $ET_A$ receptors, suggesting that antagonism of this receptor alone might be of primary therapeutic benefit. Furthermore, selective antagonism of $ET_A$ is thought to be advantageous by preserving the natural vasodilator and clearance responses induced by ET-1 through $ET_B$ receptors on endothelial cells.

Based on the results from these animal models, there are several potential clinical indications for ERAs, including pulmonary hypertension, systemic hypertension, chronic kidney disease, and restenosis following angioplasty.

Ambrisentan is (S)-2-[(4,6-dimethylpyrimidin-2-yl)oxy]-3-methoxy-3,3-diphenylpropionic acid. It is an orally active, non-sulfonamide, propanoic acid-class endothelin receptor antagonist (ERA) that is selective for the endothelin type A ($ET_A$) receptor. The S/R racemic mixture is described for example in Riechers et al., U.S. Pat. No. 7,109,205, the disclosure of which is incorporated by reference. Studies performed in human ventricular tissue with ambrisentan have demonstrated a high affinity (low $K_i$) for the $ET_A$ receptor and a >1000-fold $ET_A$ selectivity compared to the $ET_B$ receptor. Selective inhibition of the $ET_A$ receptor inhibits phospholipase C-mediated vasoconstriction and protein kinase C-mediated cell proliferation, while preserving nitric oxide and prostacyclin production, cyclic GMP- and cyclic AMP-mediated vasodilation, and endothelin-1 (ET-1) clearance that is associated with the endothelin type B ($ET_B$) receptor.

Ambrisentan has been the subject of clinical testing in humans.

Myogen, Inc. News Release, Dec. 4, 2003 (http://www.prnewswire.com/cgi-bin/stories.pl?ACCT=104&STORY=/www/story/12-04-2003/0002069898&EDATE=) announced completion of a Phase II trial of ambrisentan in PAH and initiation of Phase III trials. The release stated that the Phase III trials would evaluate 2.5 mg, 5.0 mg and 10.0 mg oral dosages of ambrisentan administered once a day.

Myogen, Inc. News Release, Jan. 8, 2004 (http://investor.myogen.com/phoenix.zhtml?c=135160&p=irol-newsArticle&ID=759080&highlight=) announced patient enrollment in phase III clinical trials of ambrisentan for treatment of PAH. According to the news release, phase II trials had demonstrated a statistically significant and clinically meaningful increase in the primary efficacy endpoint (exercise capacity measured by 6MWD) in all four ambrisentan dose groups tested.

Myogen, Inc. News Release, Feb. 16, 2004 (http://investor.myogen.com/phoenix.zhtml?c=135160&p=irol-newsArticle&ID=759478&highlight=) announced upcoming presentation of detailed results of the phase II study of ambrisentan in PAH, at the American Thoracic Society (ATS) 2004 International Conference. (Rubin (2004) "Ambrisentan Improves Exercise Capacity and Clinical Measures in Pulmonary Arterial Hypertension", ATS May 21-26, 2004.)

Myogen, Inc. News Release, May 24, 2004 (http://investor.myogen.com/phoenix.zhtml?c=135160&p=irol-newsArticle&ID=759469&highlight=) reported improvements in 6MWD, BDI and WHO functional classification seen in the Phase II study. Additionally, the news release mentioned suitability of ambrisentan for once-a-day dosing.

Myogen, Inc. News Release, Feb. 10, 2005 (http://investor.myogen.com/phoenix.zhtml?c=135160&p=irol-newsArticle&ID=759971&highlight=) announced that two abstracts describing effects of ambrisentan in patients with PAH were selected for presentation at ATS 2005 in San Diego. (Galié (2005) "Ambrisentan Long-Term Safety and Efficacy in Pulmonary Arterial Hypertension 1-Year Follow-Up", ATS May 23, 2005; Frost (2005) "Ambrisentan Improves 6MWD Comparably for WHO Class II and III PAH Patients," ATS May 22, 2005.)

Myogen, Inc. News Release, May 19, 2005 (http://investor.myogen.com/phoenix.zhtml?c=135160&p=irol-newsArticle&M=759658&highlight=) reported initiation of a clinical trial to evaluate ambrisentan in patients with PAH who have previously discontinued bosentan or sitaxsentan therapy due to liver function test (LFT) abnormalities, specifically elevated serum aminotransferase concentrations.

Rubin et al. (2005) *Future Cardiol.* 1(4):1-8 reported improvement of the mean 6MWD for all patients after 12 weeks of ambrisentan treatment, with a mean increase from baseline of 36 meters.

Galié et al. (2005) *J. Am. Coll. Cardiol.* 46(3):529-535 reported results of a randomized dose-ranging study examining efficacy and safety of ambrisentan in patients with PAH.

SUMMARY

Metabolites of ambrisentan have been identified in and determined in the human, mouse, rat, rabbit, and dog. In one aspect, the metabolites are compounds having Formula (I)

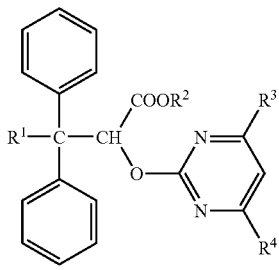

(I)

wherein R¹ is —OH or —OCH₃, R² is —H or glucuronidyl, and R³ and R⁴ are independently —CH₃ or —CH₂OH. Further, the metabolites differ in structure from ambrisentan, so that at least one of R¹, R², R³, and R⁴ is different from what it is in ambrisentan. Thus in various embodiments R¹ is —OH, R² is glucuronidyl, R³ is —CH₂OH, or R⁴ is —CH₂OH. In addition to the metabolites, synthetic compounds include compounds of Formula (I) as well as their pharmaceutically acceptable salts, solvates, hydrates, racemates, and optical isomers. In various embodiments, the metabolites are provided in isolated form, having been identified in and isolated or separated from body tissues or fluids of a test animal. In various embodiments, the compounds are provided synthetically, in solid or crystalline form, and/or in compositions of 50% purity or greater, preferably 90% purity or greater. In various embodiments, the compounds also encompass derivatives of the above metabolite structures, including hydrocarbyl ethers, lower alkyl esters, synthetic intermediates, and the like.

Optically active metabolites of ambrisentan have an S configuration around the asymmetric carbon and are represented by (II), with the same definitions as above for R¹-R⁴.

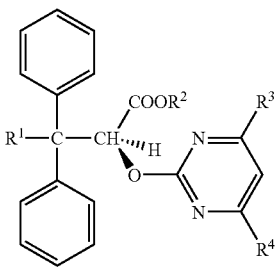

(II)

In various embodiments, metabolites of ambrisentan include an O-demethylated ambrisentan, a 4-hydroxylated ambrisentan, and a 4,6-dihydroxylated ambrisentan, as well as glucuronides of ambrisentan and the O-demethylated and hydroxylated derivatives of the glucuronides. Metabolites differing in structure from ambrisentan by being demethylated or hydroxylated at various positions are the products of so-called Phase I metabolic pathways, while metabolites of ambrisentan containing a glucuronide ester are the products of so-called phase II metabolic pathways.

Dosage forms useful for treatment of disease states include active materials selected from the compounds as well as a suitable carrier for administration to the subjects.

DETAILED DESCRIPTION

Figure 1:
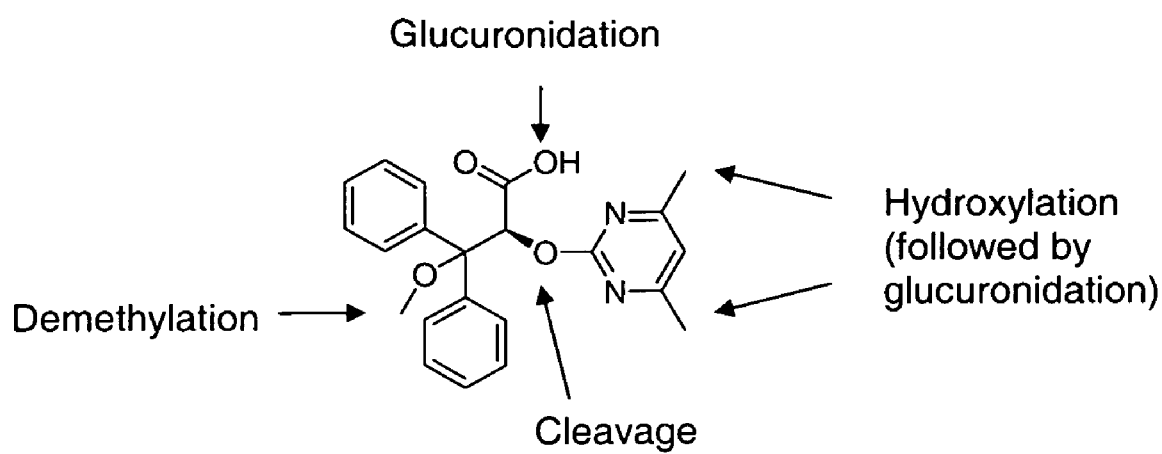
FIG. 1 gives an overview of the ambrisentan molecule (in optically active form) showing the main sites of metabolism.

The term "ambrisentan" is used herein to refer to (S)-2-[(4,6-dimethylpyrimidin-2-yl)oxy]-3-methoxy-3,3-diphenyl-propionic acid. At places, it is referred to as the ambrisentan "parent" compound solely to indicate its relation to various compounds of the invention that are described as derivatives (for example a "demethylated" ambrisentan is a derivative where a methyl has been removed). The structure of ambrisentan corresponds to structure II where R¹ is —OCH₃, R² is —H, R³ is —CH₃, and R⁴ is —CH₃. The α-carbon on the propionic acid backbone of ambrisentan is asymmetric.

In various embodiments, the invention provides compounds of general Formula (I) in isolated form

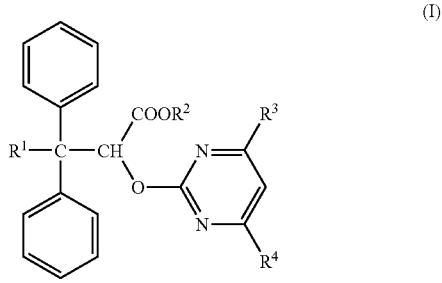

(I)

or pharmaceutically acceptable salts, hydrates, solvates, racemates, or optical isomers thereof. The compounds can exist in optically active forms (S or R configuration about the asymmetric α-carbon), in a racemic (S/R) form, or in any combination. In various embodiments the compounds serve as endothelin receptor antagonists with selective affinity for ET$_A$ receptors. In some embodiments, the structure of the compounds corresponds to metabolites produced during pre-clinical testing in non-humans and/or to metabolites produced during clinical trials in humans. Pre-clinical metabolites and clinical phase metabolites have been found and identified in various tissues, bodily fluids, and excretion media.

In Formula (I), R¹ is —OH or —OCH₃; R² is —H, lower alkyl (e.g. C₁-C₄ alkyl) or glycosidyl; and R³ and R⁴ are independently —CH₃, —C(O)H or —CH₂OR⁶, wherein R⁶ is —H or a hydrocarbyl group having 1 to 20 carbon atoms. Illustratively, when R⁶ is other than —H, it serves a protecting group of the hydroxyl, which is useful for synthesis and/or for ease of identification or of chromatographic separation and preparation. Non-limiting examples of R⁶ include methyl and benzyl. To further illustrate, when either R³ or R⁴ is —C(O)H, the compounds serve as synthetic intermediates for preparing the alcohol group —CH₂OH. At least one of R¹, R², R³, and R⁴ shows a derivatization with respect to the ambrisentan parent compound. That is to say, the novel compounds described here do not include ambrisentan itself. Thus, in various embodiments R¹ is —OH, R² is glucuronidyl, R³ is —CH₂OH, or R⁴ is —CH₂OH.

In various aspects, the glycosidyl group R² is either glucosidyl (i.e., derived from glucose) or glucuronidyl (i.e. derived from glucuronic acid), wherein hydroxyls on the glycosidyl groups are optionally acylated (for example with acetyl group —C(O)CH₃) and carboxyls on the glycosidyl group are optionally esterified with, for example, C₁-C₄ alcohols. As discussed further below, in various embodiments, the compounds correspond to products of metabolism of ambrisentan in vivo, or to synthetic intermediates useful in synthesis of the metabolites described herein.

Optically active metabolites of ambrisentan have an S configuration around the asymmetric carbon and are represented by Formula (II), with the same definitions for $R^1$-$R^4$.

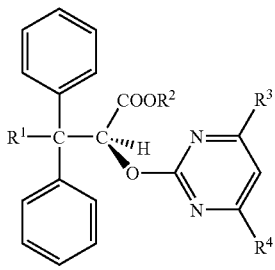

(II)

In particular embodiments, $R^1$ is —$OCH_3$ or —OH; $R^2$ is —H or glucuronidyl; and $R^3$ and $R^4$ are independently —$CH_3$ or —$CH_2OH$. In various embodiments, at least one of $R_1$, $R_2$, $R_3$, and $R_4$ is different from what it is in ambrisentan. Accordingly, in various embodiments, $R^2$ is glucuronidyl, $R^1$ is —OH, $R^3$ is —$CH_2OH$, or $R^4$ is —$CH_2OH$. It is believed that optically active metabolites result from the action of enzymes on the asymmetric starting material ambrisentan. Metabolites also include salts of compounds of Formula (II). In various embodiments, optically active compounds of Formula (II) are provided in isolated form.

In various embodiments, pharmaceutical dosage forms are provided that comprise a pharmaceutically acceptable carrier and 0.1% to 90% by weight of an active material, wherein the active material comprises at least one compound selected from those of general Formula (I)

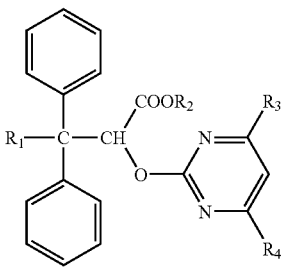

(I)

and pharmaceutically acceptable salts, hydrates, solvates, optical isomers, and racemates thereof, wherein $R^1$ is —OH or —$OCH_3$;

$R^2$ is —H, lower alkyl or glycosidyl; and $R^3$ and $R^4$ are independently —$CH_3$, —C(O)H or —$CH_2OR^6$; wherein $R^6$ is —H or a hydrocarbyl group having 1 to 20 carbon atoms;

and wherein the compound is not ambrisentan.

In one aspect, the invention provides human clinical trial metabolites of ambrisentan, illustratively in pure or isolated form. "Human clinical trial metabolites" means metabolites of ambrisentan formed in the bodies of human subjects after ingestion or application of ambrisentan according to clinical protocols regarding dosing and monitoring including those described herein. In various embodiments, the term encompasses molecular species formed in vivo, whether or not the species is detected or even analyzed for in a particular clinical trial. It is also to be contemplated that some metabolites are unique to particular individuals, reflecting different genetic make-up and the presence and activity of various enzymes, including cytochrome P450 and UGT enzymes, involved in metabolism. Human clinical trial metabolites cover all such metabolites formed in the human body.

Clinical studies on humans take on a number of forms. For example, safety, tolerability, pharmacokinetics, and pharmacodynamics are assessed in healthy subjects. Single dose pharmacokinetics are measured at oral doses of 1, 5, 10, 15, 20, 50, and 100 mg. Kinetics and dynamics are assessed over a 48 hour interval. Additionally, the effect of food on the kinetic parameters is studied in subjects who receive a dose of 50 mg both in the fasted state and after a standardized high-fat meal. Multiple dose pharmacokinetics are studied at oral doses of 5, 7.5, and 10 mg administered once daily for 10 days. Blood and urine are collected over a 24 hour interval.

Other clinical tests include crossover studies that evaluate the potential for pharmacokinetic interaction between ambrisentan and another drug. In one embodiment, the single dose pharmacokinetics of ambrisentan alone are compared with the single dose pharmacokinetics of ambrisentan administered after 7 days of administration of another drug.

Other clinical studies investigate the effect of ambrisentan in patients with pulmonary arterial hypertension. (PAH). Subjects receive doses of 1, 2.5, 5, or 10 mg once daily for 12 weeks. Liver function tests are performed periodically during the test.

In another aspect, the invention provides pre-clinical ADME metabolites of ambrisentan. "Pre-clinical ADME metabolites" means those metabolites of ambrisentan formed in vivo or in vitro during pre-clinical testing on non-human subjects. Such testing is carried out to characterize the absorption, distribution, metabolism, and excretion (ADME) of a proposed drug product prior to clinical testing on humans. Non-limiting description of such testing is provided in Examples 1-6 below.

It has been discovered that several of the compounds represented by Formulas (I) and (II) are derived from ambrisentan in mammals as the result of metabolism of the drug by so-called phase I or phase II metabolic pathways. Such designation as phase I and phase II pathways is conventional in the metabolism art and is not to be confused with the wording of Phase I and Phase II human clinical trials to support drug approval. Illustrative sites and modes of metabolism on the ambrisentan molecule are shown in FIG. 1.

In various aspects, metabolism is marked by oxidation reactions. For example, various alkyl or aryl groups are hydroxylated and/or alkoxy groups are dealkylated. These are the phase I metabolic pathways. Metabolism by phase I metabolic pathways takes place largely in the liver under the mediation of cytochrome P450 enzymes. Although all cytochrome P450 enzymes investigated are basically able to metabolize ambrisentan, the main P450 enzymes involved in ambrisentan metabolism are cytochrome P450 3A4, 3A5, and 2C19. Metabolites of ambrisentan include compounds produced by the catalytic action of cytochrome P450 enzymes or other oxidases on ambrisentan in vivo or in vitro.

Metabolites of ambrisentan include compounds produced by biosynthetic reactions of ambrisentan by the action of so called phase II metabolic pathways. For example, an important metabolic reaction of ambrisentan is the biosynthesis of acylglucuronides to form such metabolites such as A, E, and F shown below and in FIG. 2. Such was found to be involved in the metabolism of ambrisentan in rat, dog, and human hepatocytes.

The first step in the biosynthesis of acylglucuronides is the formation of β-D-glucuronide. This 1-O-acyl-β-D-glucuronide may then undergo intramolecular rearrangement by migration of the acyl group to positions C-2, C-3, and C-4 of the carbohydrate moiety. Such has been reported by Hayball in the journal Chirality, volume 7, pages 1-9 (1995).

In dog and human hepatocytes, glucoronidation is a predominant metabolic pathway. In rat hepatocytes, significant amounts of an oxidation product (e.g. Metabolite B) were also observed. These findings are in accordance with in vivo results in dog and rat. Overall, the uridine diphosphate glucuronosyl transferase enzymes UGT1A9S, UGT1A3S, and UGT2B7S were identified as the enzymes involved in metabolism. Metabolites of ambrisentan include compounds formed by the catalytic action of UGT enzymes on ambrisentan in vivo or in vitro.

Figure 2:
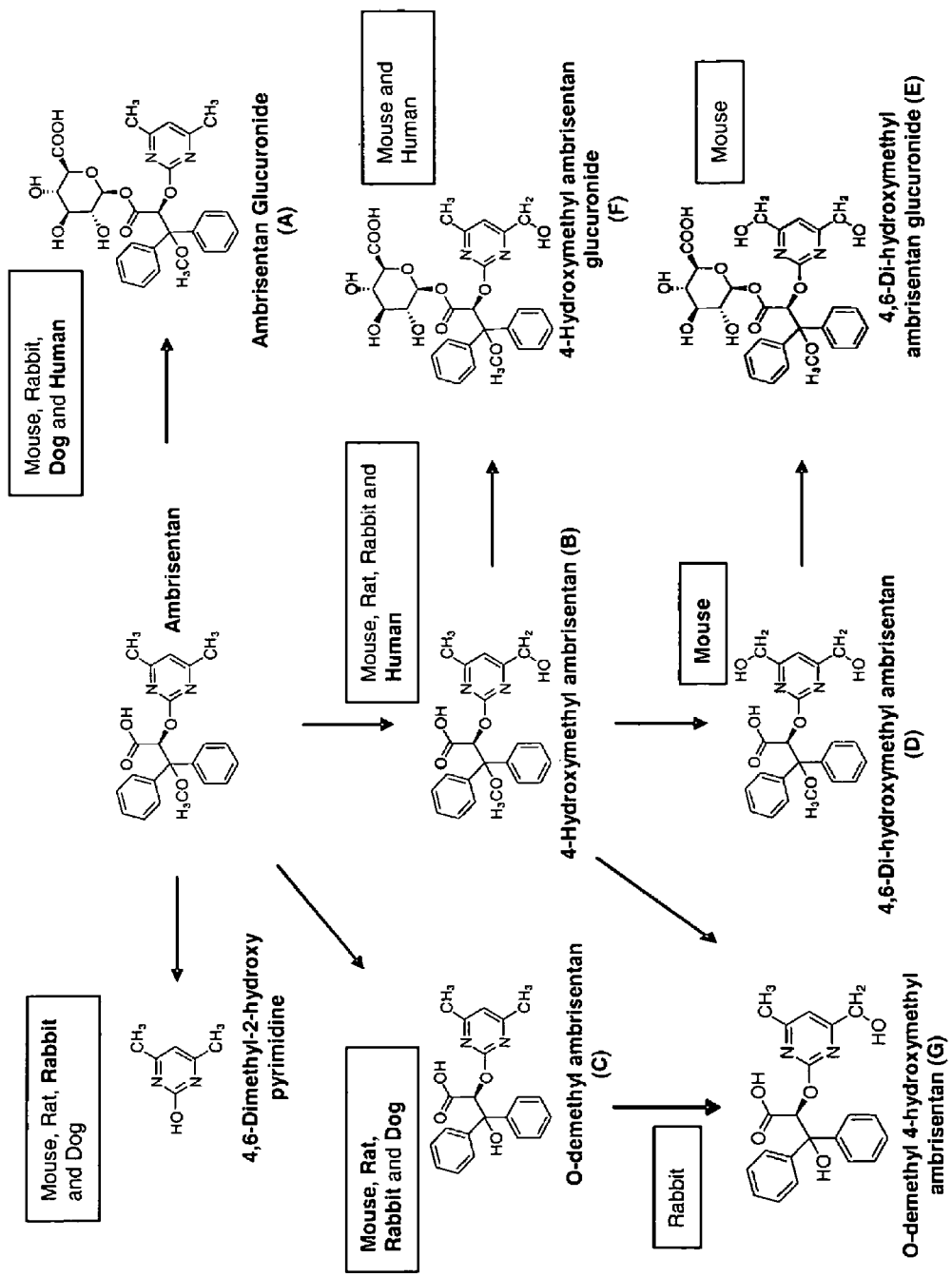
FIG. 2 gives the structure of several ambrisentan metabolites identified in a variety of mammals, including humans.

Examples of metabolites include those designated as metabolites A-G. These metabolites are shown in FIG. 2 in optically active form, with an S configuration about the asymmetric carbon as in the ambrisentan parent. Corresponding structures are shown below in Formulas (III)-(IX) in racemic form.

Metabolite A is an ambrisentan glucuronide ($R^2$ is glucuronidyl, $R^1$ is —$OCH_3$, and $R^3$ and $R^4$ are both —$CH_3$). In racemic form, compounds are represented by Formula (III):

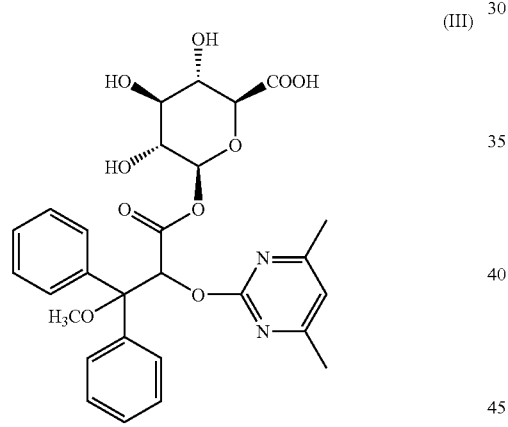

(III)

Metabolite B is a 4-hydroxymethyl ambrisentan ($R^1$ is —$OCH_3$, $R^2$ is H, one of $R^3$ and $R^4$ is —$CH_2OH$, and the other of $R^3$ and $R^4$ is —$CH_3$). In racemic form, compounds are represented by Formula (IV) and salts thereof:

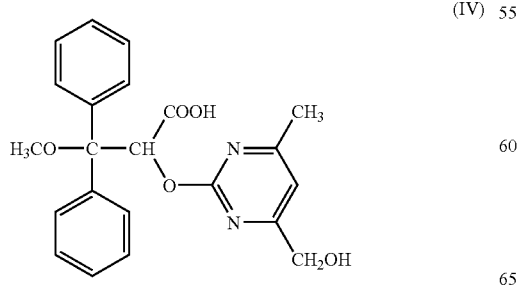

(IV)

Metabolite C is an O-demethyl ambrisentan ($R^1$ is —OH). In racemic form, compounds are represented by Formula (V) and salts thereof:

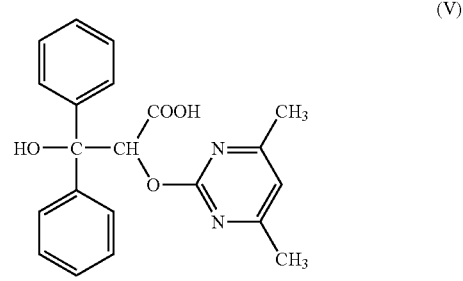

(V)

Metabolite D is a 4,6-dihydroxymethyl ambrisentan ($R^3$ and $R^4$ are both —$CH_2OH$). In racemic form, compounds are represented by Formula (VI) and salts thereof:

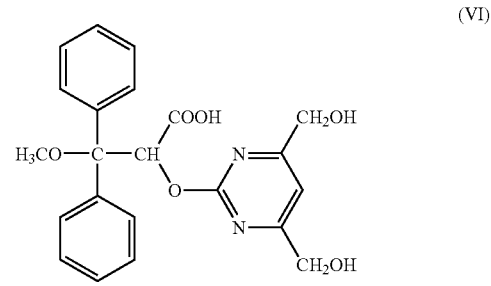

(VI)

Metabolite E is a 4,6-dihydroxymethyl ambrisentan glucuronide ($R^3$ and $R^4$ are both —$CH_2OH$ and $R^2$ is glucuronidyl). In racemic form, compounds are represented by Formula (VII) and salts thereof:

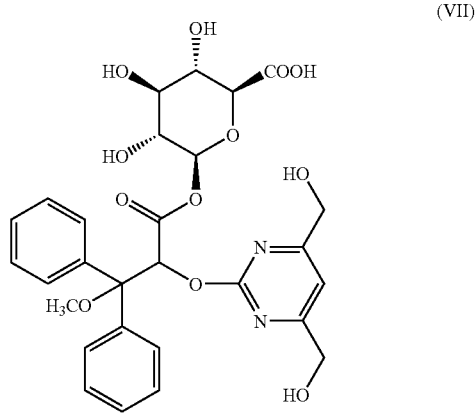

(VII)

Metabolite F is a 4-hydroxymethyl ambrisentan glucuronide (one of $R^3$ and $R^4$ is —$CH_2OH$— the other is —$CH_3$— and $R^2$ is glucuronidyl). In racemic form, compounds are represented by Formula (VIII) and salts thereof:

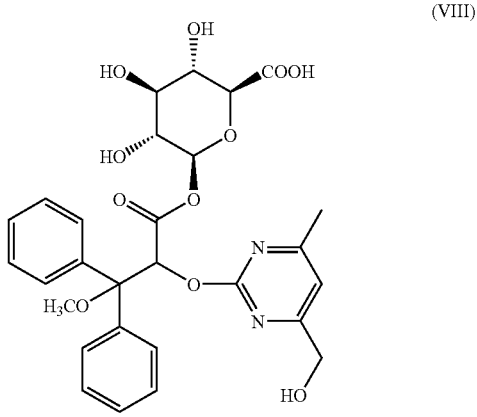

(VIII)

Metabolite G is an O-demethyl 4-hydroxymethyl ambrisentan ($R^1$ is —OH and $R^3$ is —$CH_2OH$). In racemic form, compounds are represented by Formula (IX) and salts thereof:

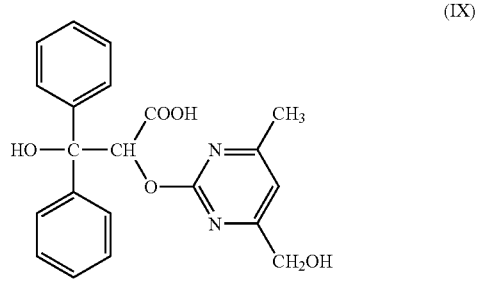

(IX)

In various embodiments, ambrisentan metabolites—including metabolites A, B, C, D, E, F, and G—and compounds with the Formulas (III)-(IX) above are isolated from body tissues and fluids, and/or prepared synthetically. A variety of chromatographic separation processes—such as gas chromatography, liquid chromatography, and thin layer chromatography (TLC)— can be carried out on the tissue and fluid samples to provide test samples for further analysis, such as by nuclear magnetic resonance or mass spectrometric analysis. In such samples, the metabolites are contained in compositions that are essentially lacking in the presence of any of the other metabolites. In such cases, the presence of a metabolite in a sample can be quantified by physical methods such as the measurement of nuclear decay from radioactive isotopes, by measurement of index of refraction, by flame ionization, by ionization and deflection in magnetic fields such as in mass spectrometry, and the like.

In various embodiments, the compounds and metabolites are provided in crystalline or solution form having a considerable degree of purity. Organic synthetic routes are available for preparing the compounds in relative pure form, for example in purities of 80% or greater, 90% or greater, 95% or greater, and 99% or greater. Recrystallization and other purification methods can be carried out to provide compounds that are essentially 100% pure. Such synthetic methods and purification techniques are known in the art and are illustrated in non-limiting fashion in the Examples that follow.

In various embodiments, the compounds are provided in substantially pure form. Substantially pure means that the compounds are pure enough for FDA approval and contain essentially no contaminants or other materials, or alternatively a level of impurity that does not adversely or unacceptably affect the properties of the compounds as regards safety, effectiveness, stability, and other desirable properties.

Methods of the invention include administering ambrisentan or an ambrisentan metabolite to a mammal and detecting metabolites by measuring the level or concentration of one of the metabolites in the tissues or bodily fluids of the mammal. Bodily fluids include without limitation blood plasma, bile, urine, and feces, while tissues include without limitation liver microsomes, hepatocytes, and perfused livers. In various embodiments, the metabolites are labeled with various isotopes to assist in the detection or quantification of the metabolites in the tissues or bodily fluids. Thus, the metabolites include those that are labeled with $^{14}C$ or tritium ($^3H$) for the purpose of detecting or identifying species from their nuclear decay products, as well as metabolites labeled with $^{13}C$ or deuterium ($^2H$) to facilitate nuclear magnetic resonance and/or mass spectrometric analysis of the compounds. As used herein, deuterated means substituted with deuterium ($^2H$) and tritiated means substituted with tritium ($^3H$).

In various embodiments, the compounds exhibit an antagonistic binding to $ET_A$ and $ET_B$ receptors, and are selective for the $ET_A$ receptor. In some embodiments they exhibit an affinity for $ET_A$ that is at least about 50-fold and preferably greater than or equal to about 100-fold more sensitive than that for $ET_B$. In various embodiments, the selectivity for $ET_A$ holds even though $K_i$ and $IC_{50}$ values for the metabolites tend to be higher, by as much as an order of magnitude or so, than the parent ambrisentan. To illustrate, compared to the results for ambrisentan parent compounds in Chinese hamster ovary cells with an incubation time of 30 minutes, metabolites B and C show 35 to 64 fold weaker affinity for the $ET_A$ receptor and 11 to 84 fold weaker affinity for the $ET_B$ receptor than the parent substance ambrisentan, while the affinity of metabolites B and C for the $ET_A$ receptor is about 100 times that for the $ET_B$ receptor.

In various embodiments, compounds of the invention, including metabolites A, B, C, D, E, F, and G as well as their salts, optical isomers, racemates, tautomers, and isotopically labeled variants (including $^{14}C$, $^{13}C$, tritium, and deuterium substituted variants) are formulated into suitable dosage forms for administration to humans or other mammals. In some embodiments, for example, the compounds of the invention may exhibit favorable toxicological profiles in comparison to conventional therapy or therapy with the parent compound.

As selective endothelin receptor antagonists, in various embodiments the compounds of the invention are used to treat such conditions as pulmonary hypertension, systemic hypertension, chronic kidney disease, and restenosis following angioplasty. Thus they are administered in preferred embodiments to subjects having a disease state for which ERAs, including selective endothelin receptor antagonists like ambrisentan, are indicated. Alternatively or in addition, they are administered to subjects or test animals not having the disease states for the purpose of studying non-pharmacological effects such as side effects, toxicity, metabolism, uptake, bioavailability, and routes of excretion.

In various embodiments, the compounds are administered by any suitable route including oral, rectal, intranasal, intrapulmonary (e.g., by inhalation), or parenteral (e.g. intradermal, transdermal, subcutaneous, intramuscular or intravenous) routes. Oral administration is preferred in some embodiments, and the dosage can be given with or without food, i.e. in the fasting or non-fasting state. Non-limiting examples of dosage forms include uncoated or coated tablets, capsules, powders, granules, suppositories, solutions, ointments, creams, and sprays.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. In one embodiment acid hydrolysis of the medicament is obviated by use of an enteric coating.

An enteric coating is a means of protecting a compound of the invention in order to avoid exposing a portion of the gastrointestinal tract, typically the upper gastrointestinal tract, in particular the stomach and esophagus, to the compound of this invention. In this way gastric mucosal tissue is protected against rates of exposure to a compound of the invention which produce adverse effects such as nausea; and, alternatively, a compound of the invention is protected from conditions present in one or more portions of the gastrointestinal tract, typically the upper gastrointestinal tract.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

In various embodiments the compounds are formulated in a carrier system. Such systems are known and include binders, fillers, preservatives, disintegrants, flow regulators, plasticizers, wetting agents, emulsifiers, dispersants, lubricants, solvents, release slowing agents (including enteric coatings), antioxidants, and propellant gases. Especially when formulated for administration to humans, the actives are preferably combined with at least one pharmaceutically acceptable carrier. Such carriers are known and include without limitation cellulose derivatives, polyethylene glycol, and N-vinylpyrrolidone polymers. The administration forms comprise a therapeutically effective amount of the compounds, which make up from 0.1% to about 90% by weight of the dosage form.

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextrin, hydroxyalkylcellulose, hydroxyalkylmethylcellulose, stearic acid and the like.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Metabolites A, B, C, D, E, F, and G have been detected in various tissues and body fluids of mouse, rat, rabbit, dog, and humans. A summary of the findings, showing the biosynthetic relationship among the metabolites and indicating in which species the presence of the metabolite is significant, is given for illustration in FIG. 1.

In other embodiments, a cleavage product of ambrisentan is formed upon metabolism. The cleavage product, observed in mouse, rat, rabbit, and dog, is the known compound 4,6-dimethyl-2-hydroxypyrimidine.

EXAMPLES

Example 1

In Vitro $ET_A$ and $ET_B$ Receptor Binding of Ambrisentan Metabolites

The in vitro binding activity of 2 metabolites of ambrisentan, Metabolite B (a hydroxylated derivative) and Metabolite C (an O-demethylated derivative), is evaluated against human $ET_A$ and $ET_B$ receptors expressed in CHO cells. The test compounds are dissolved at $10^{-2}$M in methanol: Cremophor EL® 100:1 and diluted in deionized water to concentrations of $10^{10}$ to $10^{-6}$ M. Binding reactions are initiated by addition of [$^{125}$I]-labeled ET-1 or [$^{125}$I]-labeled ET-3 for the $ET_A$ and $ET_B$ receptors, respectively, after 2 minutes preincubation of the membranes in the presence of Metabolite B or Metabolite C. The specific radioligand binding to each receptor is calculated as the difference between total binding and non-specific binding, determined in the presence of an excess of unlabeled ET-1. IC; values are determined by nonlinear curve fitting from experiments performed with 3 concentrations of test compound. The concentration required for 50% inhibition of radioligand binding ($IC_{50}$) is determined by nonlinear regression based on percent displacement and $K_i$ is calculated based on $IC_{50}$ values. These studies are performed with incubation times of 30 minutes, rather than under steady-state conditions for ambrisentan. Results are given in Table 1

TABLE 1

K$_i$ Values of Ambrisentan and its Metabolites
B and C for the ET$_A$ and ET$_B$ Receptors

| Substance | K$_i$[nM] ± SE | |
|---|---|---|
| | ET$_A$ | ET$_B$ |
| Ambrisentan | 0.63 ± 0.2 | 48.7 ± 1.17 |
| Metabolite B | 40.3 ± 6.1 | 4099 ± 322 |
| Metabolite C | 22.2 ± 4.2 | 556 ± 43.6 |

Example 2

In Vitro Metabolism in Liver Microsomes and Hepatocytes

The in vitro metabolism of ambrisentan is investigated in liver microsomes and hepatocytes of rats, dogs, and humans.

In rat, dog, and human liver microsome studies targeting phase I metabolism, a hydroxylated metabolite (Metabolite B) of ambrisentan is observed. However, turnover of ambrisentan parent compound to this metabolite is low (3-4%), indicating that phase I metabolism contributes minimally to ambrisentan metabolism.

In dog and human hepatocytes, phase II metabolism is the preferred route, with 25% and 21% of radiolabeled ambrisentan being metabolized by this pathway over a 24-hour period. The primary metabolite identified is an acylglucuronide (Metabolite A) of ambrisentan parent compound, with only trace amounts (<1%) of a hydroxylated metabolite detected. Phase II metabolism occurs to a lesser extent in rat hepatocytes with 15% being metabolized over a 24-hour period, and a significant amount of a phase I hydroxylated metabolite (metabolite B) also formed.

Reaction phenotyping using microsomes expressing single CYP isoenzymes or uridine diphosphate glucuronosyl transferase (UGT) isoenzymes are used to identity those enzymes that are sufficient to metabolize ambrisentan in vitro. Results from these experiments indicate that ambrisentan can be glucuronidated via several UGT isoenzymes (UGT1A9S, UGT2B7S, and UGT1A3S) and oxidatively metabolized via several CYP isoenzymes (CYP3A4, CYP2C19, and CYP3A5).

Example 3

Liver Perfusion Study in Rats

The metabolic pathways of ambrisentan in male Wistar rats are investigated using the isolated perfused rat liver model. [$^{14}$C]-labeled ambrisentan is used as the radiolabeled drug at perfused doses of 0.058 and 0.052 mg/g liver, 0.186 and 0.199 mg/g liver, and 0.616 and 0.556 mg/g liver (corresponding to doses of 3, 10, and 30 mg/kg, respectively). The livers are removed from 2 animals in each dose group and perfused in a recirculating system for 6 hours and the metabolite pattern of the perfusion medium and bile determined.

Six hours post-dose, the levels of total radioactivity in the perfusate decrease by 55% for the 3 mg/kg dose and 10 mg/kg doses and 45% for the 30 mg/kg dose. During the same period of time, the cumulative excretion of total radioactivity in the bile is 25% (3 mg/kg dose), 30% (10 mg/kg dose), and 31% (30 mg/kg dose).

In various embodiments, metabolites are separated by an HPLC method, and their structures are determined by liquid chromatography/mass spectrometry techniques. Metabolic products include compounds of C-oxidation (phase I metabolic pathway) and of conjugation with glucuronic acid (phase II metabolic pathway). Saturation of the C-oxidation reaction did not occur. The metabolite pattern is similar in the perfusate and bile, with 4 peaks that are identified as 1) unchanged parent compound, 2) parent glucuronide (Metabolite A), 3) a hydroxylated derivative of the parent compound (Metabolite B), and 4) a glucuronide of the hydroxylated metabolite (Metabolite F). Parent compound is the predominant peak at all doses tested in the perfusate, and at 10 mg/kg and 30 mg/kg in the bile. At the 3 mg/kg dose, parent glucuronide is the predominant peak in the bile. Additionally, traces of 2 more metabolites are detected in the bile. These metabolites are formed by oxidative cleavage of the methyl group and by hydroxylation of one of the methyl groups of the pyrimidine ring and by conjugation with glucuronic acid.

Example 4

In Vivo Metabolism of Ambrisentan

In vivo hepatic metabolism studies in mouse, rat, rabbit, and dog indicate that unchanged parent compound predominates in the plasma, urine and feces. Metabolites identified in all animal species included an acylglucuronide of ambrisentan parent compound (Metabolite A), an O-demethylated derivative (Metabolite C), a hydroxylated derivative (Metabolite B), a dihydroxylated derivative (Metabolite D), and 4,6-dimethyl-2-hydroxypyridine. Three of these 5 metabolites are observed in the human in vitro studies (microsomes and hepatocytes), and there are no metabolites observed in the human in vitro studies that are not observed in the 4 animal species tested.

Example 5

In Vivo Excretion

Following active transport across the hepatocyte membrane, ambrisentan is secreted into the bile canaliculi and is excreted via the bile into the feces.

The excretion of ambrisentan and its metabolites is assessed in rats following iv administration of a single 10 mg/kg dose of ambrisentan and in dogs following administration of a single 3 mg/kg oral dose of ambrisentan. In both studies, the major route of excretion is via feces. Recovery of radiolabeled compound in the rat study averages 88% in the feces, and 9% in the urine. Recovery of radiolabeled compound in the dog study averaged 90% in the feces and 8% in the urine. In both animal models, the majority of radiolabeled compound is excreted within the first 24 hours following administration.

In the dog study, unchanged substance dominated in the feces and urine. The parent compound glucuronide (Metabolite A) is the main metabolite in feces. The main metabolite in urine is the cleavage product of ambrisentan (4,6-dimethyl-2hydroxypyrimidine).

Example 6

Biliary Excretion

The biliary excretion and enterohepatic circulation of ambrisentan and its metabolites is assessed in anesthetized male rats after intraduodenal administration of radiolabeled ambrisentan. Bile and urine are collected over a 24-hour period. Within 24 hours of dosing, 94.8% of total radioactivity is recovered from the bile, and 1.5% from the urine. The high recovery in bile indicates that absorption occurs almost entirely in the intestine. To assess enterohepatic circulation, a second set of rats (acceptor rats) is intraduodenally dosed with pooled bile (0-12 hour period) from the first set of rats (donor rats), and bile and urine are again collected over a 24-hour period. Following dosing with bile, 76.5-94% of total radioactivity is recovered in the bile of acceptor rats, indicating a high enterohepatic circulation of ambrisentan and its metabolites. The metabolite patterns in bile from donor and acceptor rats are similar.

Radiolabeled ambrisentan (10 mg/kg) is administered to dogs intraduodenally to assess the extent of biliary excretion and to identify ambrisentan metabolites in the bile. Eight hours post-administration, 54% and 47% of total radioactivity is excreted into the bile in males and females, respectively. Of this, an ambrisentan parent glucuronide (1-O-acylglucuronide) (Metabolite A) is the predominant metabolite, representing 77%-81% of the total radioactivity.

The acylglucuronide parent compound (Metabolite A) is the predominant metabolic species in the bile, but the parent compound is the predominant metabolic species in the feces. This suggests that the acylglucuronide bond of the acylglucuronide parent compound is cleaved in the feces, releasing ambrisentan parent compound. This enzymatic cleavage is most likely due to the intestinal microflora. In contrast, biliary excretion and ADME studies in rats indicate that ambrisentan parent compound is the predominant metabolic species in both bile (95%) and feces (ca. 80%).

Examples 7-19

Synthesis of Compounds

Unless stated otherwise reactions are conducted at ambient temperature and pressure, and mixing is by magnetic stirring under an atmosphere of dry nitrogen. Organic extracts are combined and dried with anhydrous sodium sulfate, then filtered and the filtrate concentrated under reduced pressure using a rotary evaporator.

Spectroscopic data are consistent with the structures and names. Illustrative data are given in some of the Examples. Examples 7-19 provide syntheses of various optically active compounds, prepared by starting with ambrisentan, which has an absolute S configuration at the alpha (2-) carbon. Racemic compounds and R-compounds are prepared analogously, beginning with racemic (S/R)-2-[(4,6-dimethylpyrimidin-2-yl)oxy]-3-methoxy-3,3-diphenylpropionic acid and (R)-2-[(4,6-dimethylpyrimidin-2-yl)oxy]-3-methoxy-3,3-diphenylpropionic acid, respectively. The ambrisentan compound starting material for the following examples is synthesized according to known procedures, for example by racemic resolution of a 3-methoxy-3,3-diphenyl-2-hydroxypropanoic acid intermediate (or its methyl ester) with subsequent etherification to the optically active ambrisentan, or by a classical racemate separation of a racemic 2-[(4,6-dimethylpyrimidin-2-yl)oxy]-3-methoxy-3,3-diphenylpropionic acid carried out using with suitable enantiomerically pure bases. Synthesis of ambrisentan and related compounds has been reported in the literature, for example in Riechers et al., Journal of Medicinal Chemistry, vol. 39, pp. 2123-2138 (1996); Drugs of the Future 2005, 30(8), 765-770; Jansen et al., Organic Process R&D (2001) 5, 16-22; and Riechers et al. WO 1996/11914 published 25 Apr. 1996, the disclosures of which are useful as background information and are incorporated by reference.

Example 7

(2S,3R,4S,5S,6S)-24(S)-2-(4,6-Dimethylpyrimidin-2-yloxy)-3-methoxy-3,3-diphenylpropanoyloxy)-6-(methoxycarbonyl)tetrahydro-2H-pyran-3,4,5-triyl triacetate

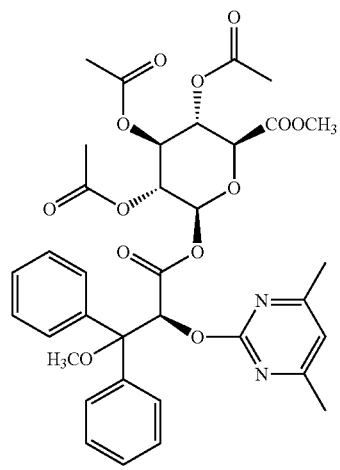

A mixture of (S)-2-(4,6-dimethylpyrimidin-2-yloxy)-3-methoxy-3,3-diphenylpropanoic acid (hereinafter "ambrisentan", 1.9 g, 5.0 mmol) and potassium carbonate (0.83 g, 6.0 mmol) in acetonitrile (30 mL) is stirred for 0.5 hr. (2R,3R,4S,5S,6S)-2-Bromo-6-(methoxycarbonyl)tetrahydro-2H-pyran-3,4,5-triyl triacetate (2.0 g, 5.0 mmol) is added to the reaction mixture and the reaction is stirred for 12 hr. The resulting mixture is evaporated to dryness in a rotary evaporator under reduced pressure. Water (20 mL) is added to the resulting residue and the mixture stirred for 0.5 hr yielding a precipitate. The crude product is isolated by filtration and the solid obtained washed with water (2×20 mL). The crude product is purified by recrystallization from methanol-water (2:1) to yield the title compound (1.7 g, 49%) as a white solid. MS m/z 695.2 (M$^{+\cdot}$+1).

Example 8

Metabolite A (2S,3S,4S,5R,6S)-6-((S)-2-(4,6-Dimethylpyrimidin-2-yloxy)-3-methoxy-3,3-diphenylpropanoyloxy)-3,4,5-trihydroxytetrahydro-2H-pyran-2-carboxylic acid

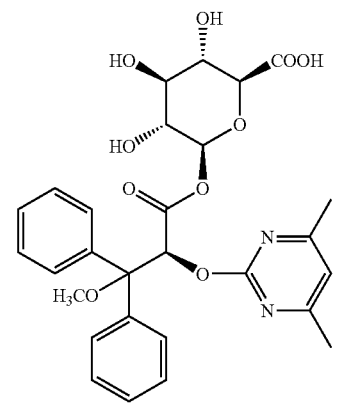

The compound of Example 7 (1.0 g, 1.44 mmol) is dissolved in methanol (87 mL) and then triethylamine (25 mL) is added. Water (25 mL) is slowly added to the reaction solution and the reaction stirred 0.5 hr longer. Volatiles are evaporated from the finished reaction under reduced pressure. The resulting mixture is adjusted to pH ~2 with 2N HCl at 0-5° C. and then extracted with ethyl acetate (2×15 mL). The yield of crude product is 600 mg. A portion of the crude product (200 mg) is purified by preparative HPLC to yield the title compound (80 mg, 30%). MS m/z 555.1 ($M^{+\cdot}$+1); $^1$H NMR (CDCl$_3$, 200 MHz) δ 5.32 (C-6 pyran H, d, $J_{5,6}$=7.4 Hz); $[\alpha]_D^{20}$=−52.95° (c=1, CH$_3$OH).

Example 9

(S)-Methyl 2-(4,6-dimethylpyrimidin-2-yloxy)-3-methoxy-3,3-diphenylpropanoate

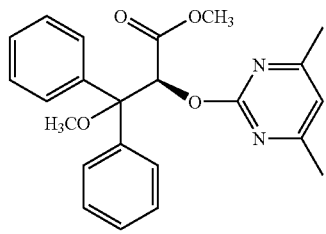

A mixture of (S)-ambrisentan (15.0 g, 40.0 mmol) and potassium carbonate (8.28 g, 60.0 mmol) in acetone (100 mL) is stirred for 0.5 hr. Methyl iodide (3 mL, 47.0 mmol) is slowly added drop-wise and then the reaction mixture is stirred for 3 hr. The resulting mixture is concentrated to dryness under reduced pressure. The residue is mixed with water (100 mL) and extracted with ethyl acetate (4×100 mL). The yield of the title compound is 15.0 g (96%). MS m/z 392.9 ($M^{+\cdot}$+1).

Example 10

(S)-Methyl 2-(4-formyl-6-methylpyrimidin-2-yloxy)-3-methoxy-3,3-diphenylpropanoate

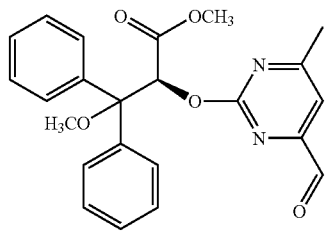

Selenium dioxide (8.5 g, 76 mmol) is dissolved in a solution of dioxane (238 mL) and water (40 mL) at 55-60° C. To the solution of selenium dioxide, the compound of Example 9 (20 g, 51 mmol) is added and then the reaction mixture is heated at reflux for 10 hr. The reaction mixture is cooled to room temperature, diluted with ether (200 mL) and filtered. The filtrate is concentrated at reduced pressure on a rotary evaporator and then extracted with ethyl acetate (2×100 mL) to yield the crude title compound. MS m/z 406.9 ($M^{+\cdot}$+1).

Example 11

(S)-Methyl 2-(4-(hydroxymethyl)-6-methylpyrimidin-2-yloxy)-3-methoxy-3,3-diphenylpropanoate

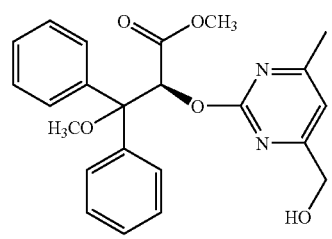

To a solution of the crude compound from Example 10 (76 mmol) in methanol (170 mL) is added sodium borohydride (1.93 g, 51 mmol) portion-wise and the reaction stirred for 3 hr. The reaction is quenched with ice-water (50 mL) and the methanol is removed under reduced pressure on a rotary evaporator. The residual aqueous phase is extracted with ethyl acetate (2×100 mL) to yield crude product (25 g). This crude product is purified by column chromatography on silica gel eluted with ethyl acetate/hexane to yield the title compound (1.8 g, 8.6%). MS m/z 409.1 ($M^{+\cdot}$+1).

Example 12

Metabolite B (S)-2-(4-(Hydroxymethyl)-6-methylpyrimidin-2-yloxy)-3-methoxy-3,3-diphenylpropanoic acid

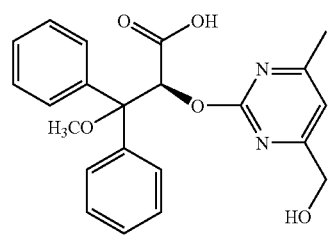

To a solution of the compound of Example 11 (0.8 g, 1.96 mmol) in methanol (10 mL) is added a solution of sodium hydroxide (0.392 g, 9.8 mmol) in water (5 mL) and the resultant mixture refluxed for 2 hr. The reaction is cooled to room temperature and the methanol is removed under reduced pressure on a rotary evaporator. The residual aqueous phase is washed with ether (2×10 mL), and then the pH of the aqueous phase is adjusted to 2-3 with 2N sulfuric acid and extracted with ethyl acetate (2×20 mL) to yield the title compound (0.6 g, 80%). MS m/z 395.1 (M⁺·+1); $[\alpha]_D^{20}$=+141.09° (c=1, CH₃OH).

Example 13

(S)-Methyl 2-(4-(benzyloxymethyl)-6-methylpyrimidin-2-yloxy)-3-methoxy-3,3-diphenylpropanoate

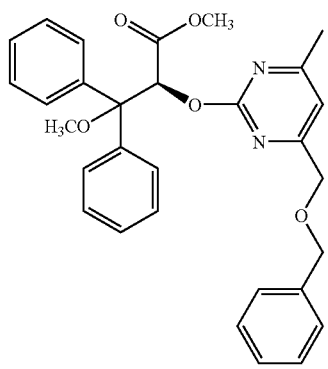

To a 0° C. mixture of lithium hydride (0.235 g, 29.4 mmol) in tetrahydrofuran and dimethylformamide (30 mL: 10 mL) is added the compound of Example 11 (3.0 g, 7.3 mmol) and the mixture stirred for 0.5 hr. Benzyl bromide (1.257 g, 7.3 mmol) is then added and the reaction stirred 12 hr at room temperature. The reaction is poured into ice-water (100 mL) and the quenched mixture extracted with ethyl acetate (2×100 mL). Concentration gives crude product that is purified by column chromatography on silica gel eluted with ethyl acetate-hexane (1:9) to yield the title compound (2.5 g, 69%). MS m/z 499.0 (M⁺·1).

Example 14

(S)-2-(4-(Benzyloxymethyl)-6-methylpyrimidin-2-yloxy)-3-methoxy-3,3-diphenylpropanoic acid

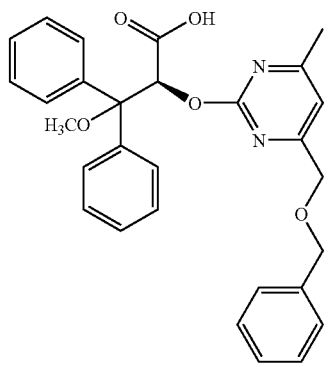

To a solution of the compound of Example 13 (1.17 g, 2.34 mmol) in methanol (20 mL) is added a solution of potassium hydroxide (0.987 g, 23.4 mmol) in water (10 mL) and the reaction stirred at reflux for 5 hr. The reaction is cooled to room temperature and the methanol removed under reduced pressure on a rotary evaporator. The aqueous residue is washed with ethyl acetate (2×25 mL) and then the pH is adjusted to 2-3 with 2N HCl. The aqueous phase is extracted with ether (2×50 mL) to yield the title compound (0.997 g, 88%).

Example 15

(2S,3R,4S,5S,6S)-2-((S)-2-(4-(Benzyloxymethyl)-6-methylpyrimidin-2-yloxy)-3-methoxy-3,3-diphenyl-propanoyloxy)-6-(methoxycarbonyl)tetrahydro-2H-pyran-3,4,5-triyl triacetate

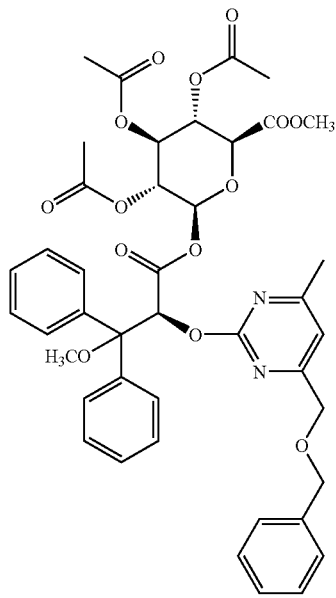

To a solution of the compound of Example 14 (0.997 g, 2.05 mmol) in acetonitrile (20 mL) is added potassium carbonate (0.284 g, 2.05 mmol) and the reaction mixture stirred for 0.5 hr. (2R,3R,4S,5S,6S)-2-Bromo-6-(methoxycarbonyl)tetrahydro-2H-pyran-3,4,5-triyl triacetate (0.817 g, 2.05 mmol) is added to the reaction mixture and the reaction stirred for 12 hr. The reaction mixture is filtered and the filtrate concentrated under reduced pressure on a rotary evaporator to give a crude product. The crude product is purified by column chromatography on silica gel eluted with ethyl acetate-hexane (2:8) to yield the title compound (1.0 g, 60%). MS m/z 801.1 (M⁺·+1); ¹H NMR (CDCl₃, 200 MHz) δ 5.65 (C-6 pyran H, d, $J_{5,6}$=8 Hz).

Example 16

(2S,3S,4S,5R,6S)-6-((S)-2-(4-(Benzyloxymethyl)-6-methylpyrimidin-2-yloxy)-3-methoxy-3,3-diphenyl-propanoyloxy)-3,4,5-trihydroxytetrahydro-2H-pyran-2-carboxylic acid

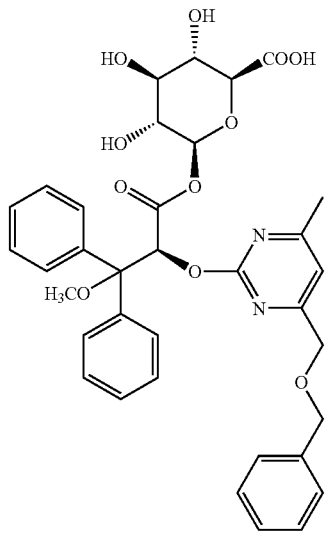

Starting with the compound of Example 15, the title compound is obtained in a similar procedure to Example 2. MS m/z 683.5 (M⁺·+Na); ¹H NMR (CDCl₃, 200 MHz) δ 5.32 (C-6 pyran H, d, $J_{5,6}$=8 Hz).

Example 17

(2S,3S,4S,5R,6S)-3,4,5-Trihydroxy-6-((S)-2-(4-(hydroxymethyl)-6-methylpyrimidin-2-yloxy)-3-methoxy-3,3-diphenylpropanoyloxy)tetrahydro-2H-pyran-2-carboxylic acid

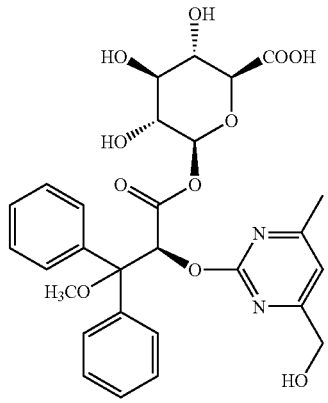

Starting with the compound of Example 16, the title compound is debenzylated by hydrogenolysis with 10% palladium on carbon under an atmosphere of hydrogen. The title compound is purified by preparative HPLC. MS m/z 570.9 (M⁺·+1); ¹H NMR (CDCl₃, 500 MHz) δ 5.35 (C-6 pyran H, d, $J_{5,6}$=8.5 Hz).

Example 18

Metabolite D (S)-2-(4,6-Bis(hydroxymethyl)pyrimidin-2-yloxy)-3-methoxy-3,3-diphenylpropanoic acid

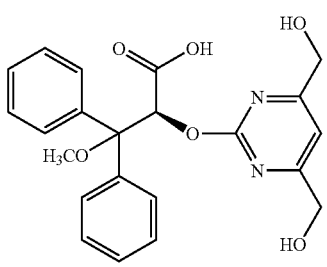

The title compound is prepared starting with the compound of Example 9 and using the procedures of Examples 9, 10, 11 and 12, except that excess selenium dioxide is used in the Example 10 procedure to prepare the dialdehyde intermediate (S)-2-(4,6-diformylpyrimidin-2-yloxy)-3-methoxy-3,3-diphenylpropanoic acid.

Example 19

Metabolite E (2S,3S,4S,5R,6S)-6-((S)-2-(4,6-Bis(hydroxymethyl)pyrimidin-2-yloxy)-3-methoxy-3,3-diphenylpropanoyloxy)-3,4,5-trihydroxytetrahydro-2H-pyran-2-carboxylic acid

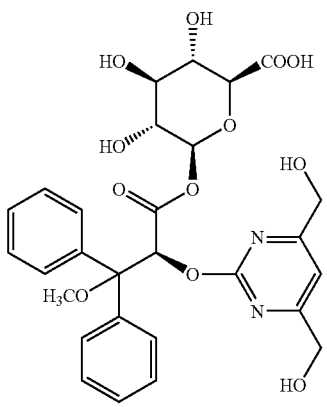

The title compound is prepared starting from (S)-methyl 2-(4,6-bis(hydroxymethyl)pyrimidin-2-yloxy)-3-methoxy-3,3-diphenylpropanoate, which is obtained as an intermediate in the preparation of Example 18, and using the procedures of Examples 13, 14, 15, 16 and 17.

We claim:

1. A method for identifying a metabolite of ambrisentan comprising: administering ambrisentan to a mammal and detecting and/or measuring a level or concentration of a metabolite of ambrisentan in tissues or bodily fluids of the mammal, wherein the metabolite comprises a compound which is selected from:

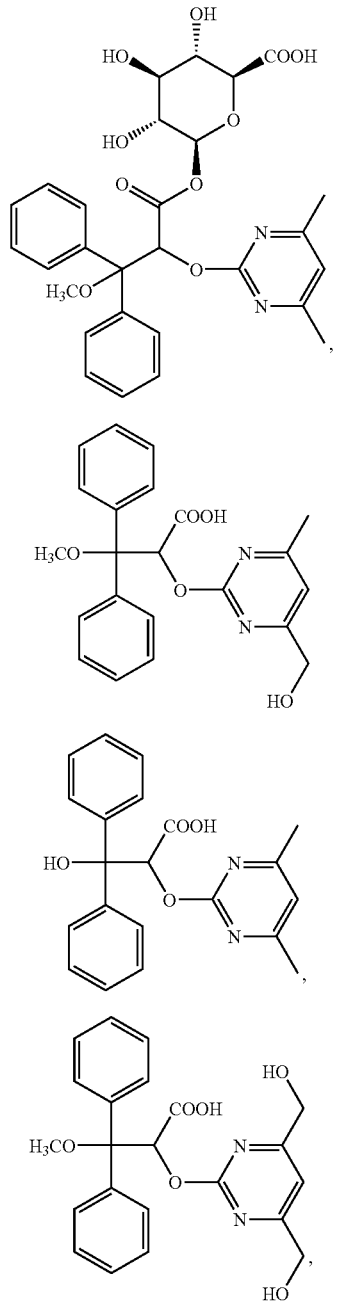

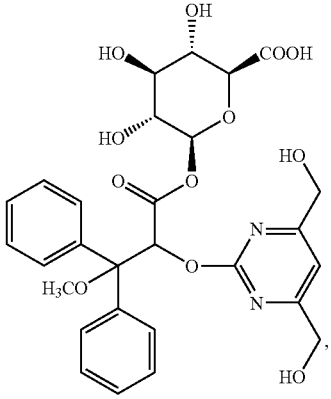

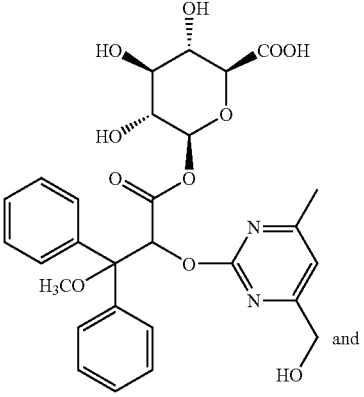

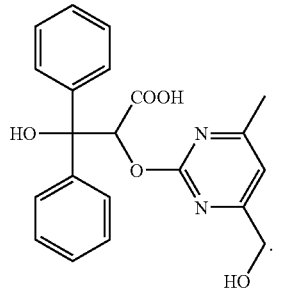

and pharmaceutically acceptable salts thereof.

2. The method according to claim 1, wherein the bodily fluids are selected from the group consisting of plasma, bile, urine, and feces.

3. The method according to claim 1, comprising detecting nuclear decay products from a $^3$H or $^{14}$C labeled ambrisentan molecule administered to the mammal.

4. The method according to claim 1, comprising administering $^{13}$C enhanced ambrisentan to the mammal.

5. The method according to claim 1, wherein the metabolite has an S configuration about the asymmetric carbon.

* * * * *

UNITED STATES PATENT AND TRADEMARK OFFICE
CERTIFICATE OF CORRECTION

PATENT NO.        : 8,217,155 B2
APPLICATION NO.   : 12/671439
DATED             : July 10, 2012
INVENTOR(S)       : Lawrence S. Melvin, Jr. et al.

It is certified that error appears in the above-identified patent and that said Letters Patent is hereby corrected as shown below:

The Specification should be amended to:

(1)   Column 13, line 36, replace "identity" with "indentify"

The Claims should be amended to:

(2)   Column 23, line 1, Claim 1, replace

"A method for identifying a metabolite of ambrisentan comprising:

administering ambrisentan to a mammal and detecting and/or measuring a level or concentration of a metabolite of ambrisentan in tissues or bodily fluids of the mammal, wherein the metabolite comprises a compound which is selected from:

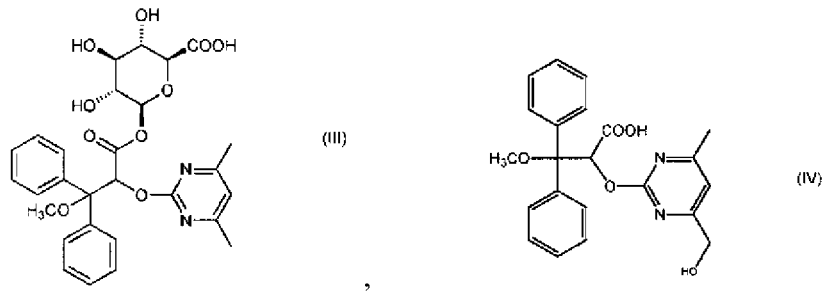

,

Signed and Sealed this
Thirteenth Day of November, 2012

David J. Kappos
*Director of the United States Patent and Trademark Office*

CERTIFICATE OF CORRECTION (continued)
U.S. Pat. No. 8,217,155 B2

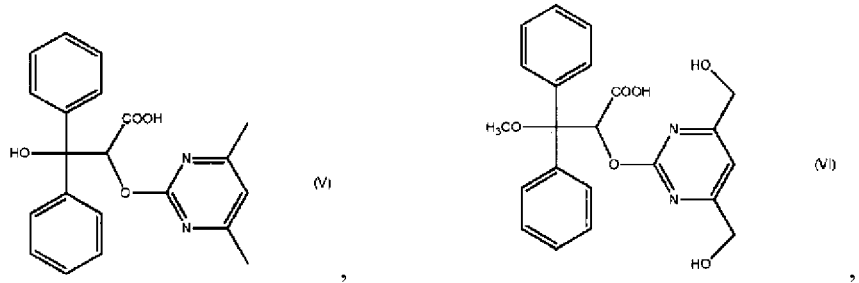

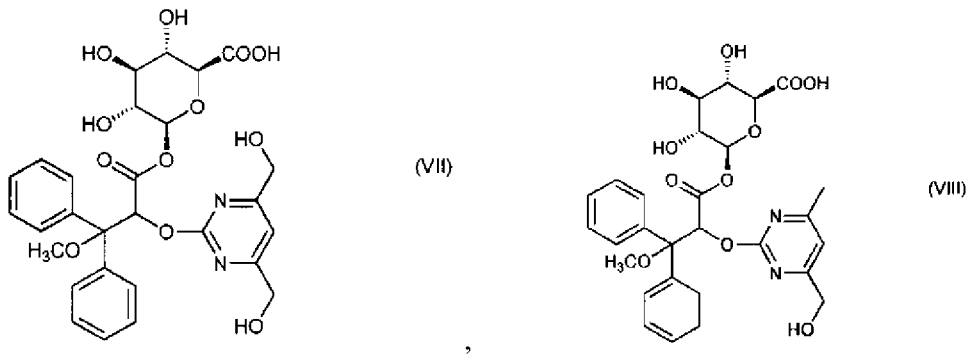

and

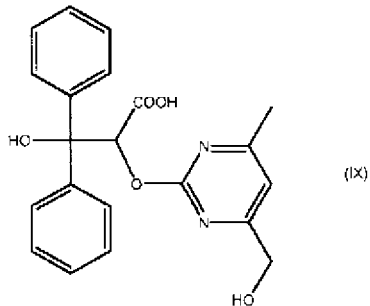

and pharmaceutically acceptable salts thereof." with

"A method for identifying a metabolite of ambrisentan comprising:

Administering ambrisentan to a mammal and detecting and/or measuring a level or concentration of a metabolite of ambrisentan in tissues or bodily fluids of the mammal, wherein the metabolite comprises a compound which is selected from:

CERTIFICATE OF CORRECTION (continued)
U.S. Pat. No. 8,217,155 B2

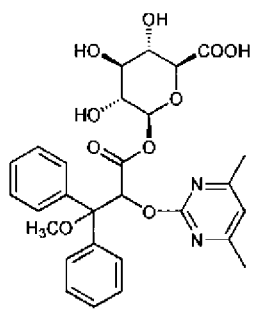
(III)

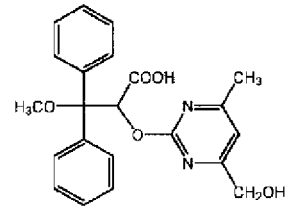
(IV)

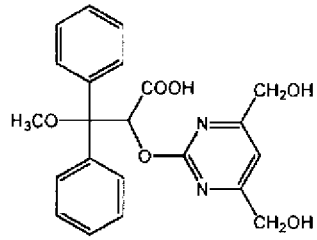
(VI)

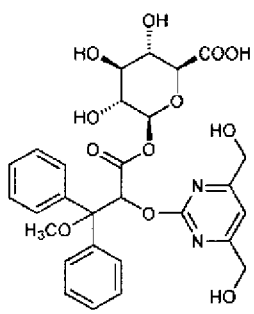
(VII)

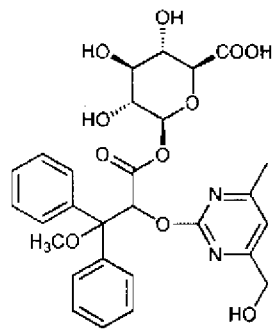
(VIII)

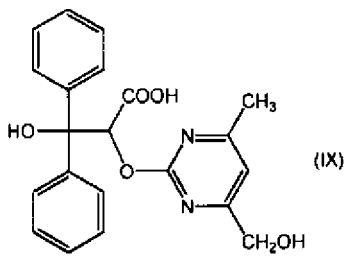
(IX)

and pharmaceutically acceptable salts thereof."